(12) United States Patent
Larsson

(10) Patent No.: US 9,211,502 B2
(45) Date of Patent: Dec. 15, 2015

(54) COVERING AND METHOD FOR TRAPPING OF EMISSIONS FROM SURFACES

(75) Inventor: Lennart Larsson, Lund (SE)

(73) Assignee: CTRAP AB, Lund (SE)

( * ) Notice: Subject to any disclaimer, the term of this patent is extended or adjusted under 35 U.S.C. 154(b) by 0 days.

(21) Appl. No.: 13/701,266

(22) PCT Filed: May 26, 2011

(86) PCT No.: PCT/SE2011/050660
§ 371 (c)(1),
(2), (4) Date: Nov. 30, 2012

(87) PCT Pub. No.: WO2011/152778
PCT Pub. Date: Dec. 8, 2011

(65) Prior Publication Data
US 2013/0071639 A1    Mar. 21, 2013

(30) Foreign Application Priority Data
Jun. 2, 2010 (SE) .................................... 1050556

(51) Int. Cl.
| | | |
|---|---|---|
| *B32B 3/26* | (2006.01) | |
| *B32B 38/00* | (2006.01) | |
| *B01D 53/82* | (2006.01) | |
| *E04F 13/00* | (2006.01) | |
| *B01D 53/04* | (2006.01) | |
| *B01D 53/22* | (2006.01) | |
| *B01J 20/20* | (2006.01) | |
| *B01J 20/24* | (2006.01) | |
| *B01J 20/26* | (2006.01) | |
| *B01J 20/28* | (2006.01) | |
| *B01J 20/32* | (2006.01) | |
| *B32B 5/02* | (2006.01) | |
| *B32B 7/02* | (2006.01) | |
| *E04B 1/92* | (2006.01) | |
| *A61L 9/00* | (2006.01) | |

(52) U.S. Cl.
CPC ............... *B01D 53/82* (2013.01); *B01D 53/04* (2013.01); *B01D 53/0407* (2013.01); *B01D 53/229* (2013.01); *B01J 20/20* (2013.01); *B01J 20/24* (2013.01); *B01J 20/26* (2013.01); *B01J 20/28035* (2013.01); *B01J 20/28038* (2013.01); *B01J 20/321* (2013.01); *B01J 20/324* (2013.01); *B01J 20/327* (2013.01); *B01J 20/3212* (2013.01); *B01J 20/3223* (2013.01); *B01J 20/3231* (2013.01); *B01J 20/3236* (2013.01); *B01J 20/3238* (2013.01); *B01J 20/3272* (2013.01); *B32B 3/26* (2013.01); *B32B 5/022* (2013.01); *B32B 7/02* (2013.01); *B32B 38/00* (2013.01); *E04B 1/92* (2013.01); *E04F 13/002* (2013.01); *A61L 9/00* (2013.01); *A61L 2209/22* (2013.01); *Y10T 29/49885* (2015.01); *Y10T 29/49888* (2015.01); *Y10T 156/10* (2015.01); *Y10T 428/2495* (2015.01); *Y10T 428/249953* (2015.04); *Y10T 428/249981* (2015.04); *Y10T 428/249982* (2015.04); *Y10T 442/60* (2015.04); *Y10T 442/681* (2015.04); *Y10T 442/69* (2015.04)

(58) Field of Classification Search
USPC .......................... 428/213, 304.4, 317.1, 316.6
See application file for complete search history.

(56) References Cited

U.S. PATENT DOCUMENTS

| | | |
|---|---|---|
| 6,083,857 A | 7/2000 | Böttger et al. |
| 2003/0012941 A1* | 1/2003 | Fujita et al. ............... C08J 3/245 428/304.4 |
| 2003/0087086 A1* | 5/2003 | Koslow et al. ................. 428/323 |
| 2003/0207635 A1* | 11/2003 | Minemura et al. ............ 442/327 |
| 2005/0252379 A1 | 11/2005 | Von Blucher |
| 2006/0024196 A1 | 2/2006 | Shimada |
| 2008/0148946 A1* | 6/2008 | Lotgerink-Bruinenberg .... 96/155 |
| 2009/0060778 A1 | 3/2009 | Close et al. |

FOREIGN PATENT DOCUMENTS

| | | |
|---|---|---|
| CN | 1114825 | 1/1996 |
| CN | 200951693 | 9/2007 |
| GB | 1166946 | 10/1969 |
| GB | 2 282 982 | 4/1995 |
| JP | 1-127743 | 5/1989 |
| JP | 10-310984 | 11/1998 |
| JP | 2001-001479 | 1/2001 |
| JP | 2003-239421 | 8/2003 |
| JP | 2003239421 A * | 8/2003 |
| JP | 3768326 | 4/2006 |
| JP | 2007014851 A * | 1/2007 |
| WO | 92/16291 | 10/1992 |
| WO | 2008/085477 | 7/2008 |

OTHER PUBLICATIONS

Machine_English_Translation_JP_2003239421_A; Miura, Hironobu; Deodorant and Moisture Absorbing Sheet Material; Aug. 27, 2003; JPO; whole document.*
Machine_English_Translation_JP_2007014851_A; Kishi, Seishichi; Porous Product; Jan. 25, 2007; JPO; whole document.*

* cited by examiner

*Primary Examiner* — Tahseen N Khan
(74) *Attorney, Agent, or Firm* — Hamre, Schumann, Mueller & Larson P.C.

(57) ABSTRACT

The present invention disclosures a covering for placement on a surface, such as a wall on the inside of a house, for reduction or prevention of a singularity or a plurality of emissions, such as harmful emissions, released from the surface. The covering comprises a trapping agent and a carrier for retaining and supporting the trapping agent, such that the trapping agent can trap the singularity or plurality of emissions without being released from the carrier. The trapping agent is a substantially irreversible trapping agent independently selected from one or several of the group consisting of absorbing agents and adsorbing agents, such that the trapping agent is capable of fully or partly trapping the singularity or plurality of emissions substantially irreversibly by absorption or adsorption, or a combination of absorption and adsorption. The covering may further comprise a semi-permeable barrier. Methods for use and manufacturing of the covering are also disclosed.

10 Claims, No Drawings

COVERING AND METHOD FOR TRAPPING OF EMISSIONS FROM SURFACES

TECHNICAL FIELD

The present invention relates to a covering for placement on a surface for reduction or prevention of emission(s) released from the surface, and to a method thereof.

BACKGROUND

Water-damage of buildings leading to dampness is common all over the world due to unsatisfactory building methods and maintenance of existing buildings. The problem is expected to increase with the global warming leading to more rain in the future in many parts of the world. Indoor dampness is related to adverse health effects and/or bad smell and has, for example, been estimated to be responsible for ca 30% of all asthma cases in the United States. The adverse effects and/or bad smell is due to various emissions from moist construction parts, e.g. wood, concrete, glue or gypsum, of the affected building. These emissions are formed in various ways as a result of the effect of water on a particular material. For example, moist cellulose or starch containing materials, e.g. wood, paper and gypsum boards provide a suitable milieu for growth of microorganisms, such as fungi or bacteria. Related volatile and semivolatile microbial products and hazardous microbial particles, constituents and/or products, such as mycotoxins or endotoxins, respectively, as well as other biologically potent microbe-associated compounds may then be emitted from such materials. Chemical reactions involving water, such as hydrolysis, may also result in the formation of various toxic, irritating and/or smelling emissions from the construction parts of a damp building. In addition, microorganisms including multidrug resistant strains may be e.g. fatal to hospitalized or immunocompromized individuals. When a building is exposed to water-damage, the people living there are often forced to be temporarily evacuated during the remediation of the building, i.e. they must be accommodated at hotels etc., which is very costly and trying for the evacuees. Additional undesired emissions, which are not necessarily related to water-damage, include e.g. emissions by chemicals used to protect building materials from degradation or in remediation of water-damaged buildings, odours and organic solvents from drying paint and monomers, or other volatile, semivolatile or non-volatile organic compounds, such as hormone disruptors.

Much effort has been devoted to the reduction of hazardous or odorous components in indoor air, such as components which are hazardous or are irritating to nose or mucous membranes.

US2009060778 (A1) discloses a method for remediation of mold in a building comprising the steps of diffusing essential oils into the building for a predetermined period of time, and directly applying a household cleaner with essential oils to any mold-affected areas.

Several compositions, e.g. boron containing products and the compositions used in US2009060778 (A1), are used to treat construction materials in buildings for the reduction of microbiological growth of e.g. mould, whereby the related emissions are simultaneously reduced. Such compositions, serving as an example of a limited way for the prevention of emissions to enter the air by inhibiting their origin does not, however, prevent emissions of microbiological activity which is not affected by the composition used, or emissions of another origin. In addition, such compositions may be odorous or may constitute, per se, or result in hazardous emissions.

WO9216291 (A1) describes a passive filter for taking up gaseous substances, preferably gaseous smelling substances, from a space. The passive filter includes a composition which includes two material components (A, B). The first material component (A) consists of one or more porous materials and the second material component (B) consists of one or more materials with the capability to take up water molecules directly from the surrounding air. After the passive filter has taken up the gaseous substance, this or the corresponding decomposition products is/are slowly emitted from the filter. Disadvantages of this filter include the release of a substance, which has initially been taken up, back to the surrounding volume, either in unchanged form or in the form of a decomposition product. People residing in the surrounding volume may, theoretically, be exposed to the same total amount of the substance in the presence of the filter, even if over a longer time period, as compared to the case when the filter is absent. Furthermore, one or several of the decomposition products may constitute a greater health hazard than the original substance.

US2006024196 (A1) discloses an indoor anti-microbial and deodorizing coating solution comprising titanium oxide and titanium phosphate. In the presence of UV light or oxygen and moisture, the titanium catalyzes chemical degradation of organic molecules whereby a deodorizing effect is achieved. Disadvantages of the use of titanium in this application include the emission of potentially hazardous chemical degradation products. Furthermore, the fire hazard of titanium in this form when combined with combustible materials, e.g. when applied on a combustible surface such as a wooden wall of a room, has not yet been fully investigated.

Furthermore, the suitability of the compositions described in US2009060778(A1), WO9216291 (A1) or US2006024196 (A1), to allow water vapour to escape from an underlying damp surface, e.g. a water-damaged wall of a house, is not fully known. Thus, the suitability of these products and compositions to cover damp surfaces for the prevention of emissions from these during their drying, such as when drying a water-damaged wall, is uncertain.

Beside ways for reduction of emissions which are already present in the indoor air, including e.g. increased ventilation or various filters through which the air is circulated, or ways for reduction of the source of emissions or chemical transformation (e.g. oxidation) or decreased release rate (e.g. as in WO9216291 [A1]) of emissions, as described above, there is a need of general ways, methods and products for the reduction or prevention of emissions to enter the adjacent surrounding, e.g. indoor air, in any form.

Hence, an improved covering and method for the reduction or prevention of emissions from a surface to enter the adjacent surrounding is desired.

SUMMARY

It is an object of the present invention, considering the disadvantages mentioned above, to provide a covering for placement on a surface which traps emissions from the surface.

It is another object of the present invention to provide a covering which traps emissions from a surface without the release of these emissions back into the surrounding air.

It is yet another object of the present invention to provide a covering which traps emissions from a surface without the release of products originating from the emissions, such as chemical decomposition products, back into the surrounding air.

These and other objects, which will appear from the following description, have now been achieved, according to one aspect of the present invention, by a covering for application on a surface and reduction or prevention of a singularity or a plurality of emissions released from the surface, the covering comprising a trapping agent and a carrier for retaining and supporting the trapping agent, such that the trapping agent can trap the singularity or plurality of emissions without being released from the carrier; wherein the trapping agent is an absorbing agent or an adsorbing agent, or a combination thereof, such that the trapping agent is capable of fully or partly trapping the singularity or plurality of emissions substantially irreversibly by absorption or adsorption, or by a combination of absorption and adsorption.

According to another aspect, the surface from which emissions are released is a solid or liquid surface.

According to yet another aspect, the carrier is sheet formed with a first side and an opposite second side, the first side is for application on the surface such that the first side is facing the surface and the second side is facing away from the surface.

According to yet another aspect, the covering is comprising a semi-permeable barrier on the second side.

According to yet another aspect, the semi-permeable barrier is sheet formed and substantially covering the surface of the second side.

According to yet another aspect, the semi-permeable barrier is porous.

According to yet another aspect, the semi-permeable barrier is substantially homogenous, such that molecules pass through the semi-permeable barrier substantially by diffusion in the material the semi-permeable barrier is made of.

According to yet another aspect, the semi-permeable barrier is made of one or several materials selected from the group consisting of different nonwoven materials (spunbound, wetlaid, spunlace, thermobonded etc) for example the materials, or modification of the materials, which are used in products such as Tyvek (a brand of flashspun polyethylene fibers), GoreTex (expanded polytetrafluoroethylene), nonwoven-based materials including air-permeable nonwowen materials such as those used for air filtration etc, cellulose, chemically modified cellulose, regenerated or modified cellulose originating from viscose, cellophane, or any other suitable polymeric or nonpolymeric material as known in the art. The semi-permeable barrier is preferably made of, but not limited to, a material that may allow passage of water vapor while at the same time being an efficient barrier (i.e. displaying a relatively low permeability in comparison to the permeability of water vapor) for liquid water, VOCs and air, or for liquid water and VOCs.

According to yet another aspect, the thickness of the semi-permeable barrier is 0.001-1 mm.

According to yet another aspect, the thickness of the semi-permeable barrier is smaller than the thickness of the carrier.

According to yet another aspect, the carrier is flexible, such that the covering attains essentially the same shape as the surface when placed thereon.

According to yet another aspect, the carrier is removable from the surface, such that the covering can be removed from the surface and such that the appearance of the surface after removal of the covering is essentially the same as the appearance of the surface before the placement of the covering thereon.

According to yet another aspect, the carrier is porous and at least a part of the trapping agent is immobilized on the inner surface of the pores of the carrier.

According to yet another aspect, the covering is permeable to water in gaseous form, such that the covering can trap the singularity or plurality of emissions while the covering is simultaneously allowing escape of water in gaseous form from the surface.

According to yet another aspect, the covering is substantially non-permeable, or permeable to only a low extent, to oxygen. The oxygen-permeability of the covering may, for example, be 1.5 to 100000 times, such as 5 to 10000 or 10 to 1000 times, less than the permeability of water or a volatile organic compound.

According to yet another aspect, the carrier is selected from one or several of the group consisting of cellulose containing materials, modified cellulose containing materials, textiles, natural or synthetic fiber materials, nanofiber materials, nonwoven materials, including for example materials which are spunbound, wetlaid, spunlace or thermobonded such as those used e.g. in Tyvek (a brand of flashspun polyethylene fibers) or GoreTex (expanded polytetrafluoroethylene), air-permeable nonwoven-based materials, such as those used for air filtration etc and porous plastic or other polymeric or monomeric materials According to yet another aspect, the covering is further comprising an adhering agent.

According to yet another aspect, the trapping agent is independently selected from one or several of the group of adsorbing agents and/or absorbing agents consisting of carbon based adsorbents, porous polymers, clays, diatomaceous earth, magnesium silicates, ashes, micronized silicon dioxide, christobalite, hydrated sodium calcium aluminosilicates, chitosan, granulas, anionic ion exchange resins, cationic ion exchange resins, modified ion exchange resins, zeolites, perlite, bentonite, $C_{4-30}$ aliphatic hydrocarbons, $C_{4-30}$ unsaturated hydrocarbons, gas chromatography stationary phases, liquid chromatography stationary phases, polyethylene glycol, silica gel, aluminum oxide, cellulose, granulates, high boiling liquids, phenyl substituted stationary phases, bases, acids and diethylene glycol succinate derivatives.

According to yet another aspect, the singularity or plurality of emissions is independently selected from one or several of the group consisting of: emissions produced by microorganisms including bacteria, fungi or mould, secondary metabolites of the microorganisms, emissions from paints, emissions from surfaces which have been exposed to smoke from fire or tobacco smoking, emissions known or suspected to act as hormone disruptors or by other means known or suspected as being harmful, emissions consisting of particles of microorganisms, degradation products of construction materials which are unrelated to growing microorganisms, emissions resulting from treating building materials with chemicals for preservation (e.g. cuprinol and similar substances) or remediation after water-damage (borate, bleach etc), emissions having an unpleasant odour, irritating or unpleasant compounds, toxins, emissions formed upon the action of water on impregnated wooden materials, emissions formed by hydrolysis of glues and plasticizers, emissions occurring in water damaged buildings, emissions that originate either from growing microorganisms or from water acting on building materials such as emissions resulting from one or several secondary reactions, aldehydes, terpenes, furans, glycol ethers, ketones, alcohols, sulfides, disulfides, organic compounds with a molecular weight in the range from 16 to 1500 g/mol, allergens, and compounds or particles which are odorous, irritating or harmful to the health of humans or animals.

According to one aspect, a method is provided for reduction or prevention of a singularity or a plurality of emissions released from a surface, the method comprising the steps of: applying, fastening or adhering an absorbing agent or an adsorbing agent to said surface; and adsorbing or absorbing the emissions substantially irreversibly, by absorption or adsorption, or by a combination of absorption and adsorption, in the absorbing agent or in the adsorbing agent.

According to another aspect, a method is provided wherein the absorbing agent or the adsorbing agent is applied, fastened or adhered to the surface together with a carrier for retaining and supporting the trapping agent.

According to yet another aspect, the method is further comprising applying, fastening or adhering a semi-permeable barrier to the carrier on the side of the carrier which is opposite the side of the carrier which is for facing the surface.

According to yet another aspect, a method is provided wherein the surface is an inner surface or a part of an inner surface of a construction used to house or shelter humans or animals, or the surface is an inner surface or a part of an inner surface of a construction which is linked to an accommodation for humans or animals, such that the emissions can pass between the construction and the accommodation when released into the space encompassed by the construction.

According to one aspect, a method for the manufacturing of a covering is provided, comprising the step of: (i) coating the surface of the carrier with a dry composition comprising the trapping agent, or with a suspension or solution of the trapping agent in a solvent or liquid.

According to another aspect, the dry composition or the suspension or solution further comprise an adhering agent.

According to yet another aspect, step (i) is followed by an additional step of: (ii) evaporating the solvent or liquid, such that the trapping agent becomes adhered to the carrier.

According to one aspect, a method for the manufacturing of a covering is provided, comprising the steps of: (i) coating the surface of the carrier with an adhering agent; and (ii) spreading the trapping agent on the surface of the carrier, such that the trapping agent adheres thereon. The trapping agent may also be impregnated onto the carrier.

According to one aspect, the method is comprising an additional step of applying, fastening or adhering a semi-permeable barrier to the carrier, the additional step being carried out before step (i), or after step (i) and before step (ii), or after step (ii).

Further features of the invention and its embodiments are set forth in the appended claims.

DETAILED DESCRIPTION OF THE EMBODIMENTS

Embodiments of the present invention will be described in more detail below in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments is not intended to be limiting of the invention.

Herein the phrases "emission" or "emissions" are meant to be understood as gases, vapors, finally divided solids, liquid aerosols, solid aerosols, particles, organic compounds, inorganic compounds, and the like, of microbiological or other origin, that is/are either harmful to the health of humans or animals or, for any other reason, its/their presence in the air of an accommodation for humans or animals normally is/are undesired. The phrases "emission" or "emissions" are not meant to be understood as comprising benign normally occurring constituents of what is generally considered as clean healthy air, for example water vapor and carbon dioxide.

The present invention discloses a covering for placement on a surface for reduction or prevention of a singularity or a plurality of emissions released from the surface. The surface may be a solid surface such as, for example, a wall of a building. In addition, emissions originating from liquid surfaces or from cavities, chinks etc, may also be reduced or prevented by the covering. The covering may, for example, be attached at an adjacent solid surface so that the covering covers a surface above the liquid surface, cavity or chink. When placed thereon, the covering may fully or partly trap one or several of these emissions to prevent them from reaching the adjacent space, such as e.g. indoor air. The emissions may consist of various components, including compounds or particles which are due to growing microorganisms, such as mould or bacteria. Additional components include degradation products of construction materials which are unrelated to growing microorganisms, or chemical emissions resulting from treating the construction materials with chemicals for the purposes of preservation (e.g. cuprinol and similar substances) and/or remediation after e.g. water damage (e.g. borate or bleach). Furthermore, the emissions may comprise compounds formed through secondary reactions between different emitting substances, or between emitting substances and other compounds present in the environment. The covering is preferably arranged to trap such emissions which are harmful to the health of humans or animals, and/or which are irritating to nose or mucous membranes. The covering may also be arranged to trap emissions which have an unpleasant odour. The covering comprises essentially a trapping agent and a carrier. The carrier is retaining and supporting the trapping agent. The trapping agent may thus trap the emissions without being released from the carrier. The covering may further comprise a semi-permeable barrier. This barrier may be placed such that the carrier and the trapping agent are located in between the surface, from which the emissions are released, and the barrier. Such a barrier may increase the efficacy of the covering to trap emissions.

The covering may be permeable to water in gaseous form to allow drying of the underlying surface, such as a wall, a floor, or a ceiling of a house. Water-damaged walls, floors or ceilings of a house may thus be applied with the covering of the invention to allow drying of these building parts with simultaneous prevention of emissions, such as for example emissions related to mould. Advantageously, people may reside in the house, for example while the drying is carried out, without being exposed to hazardous or uncomfortable levels of the emissions and without the need to evacuate. In addition, it may be unnecessary to replace water-damaged building materials, since drying may be enough, because the covering will prevent the release of harmful emissions during or after the drying. The covering may be provided with a "hostile" chemical such as NaOH or a boron containing composition for the prevention of mold growth. This is useful for application in, for example, crawlspaces. Nowadays, expensive dehumidifiers are frequently installed in crawlspaces to prevent mould growth. The covering of the invention will then, in many cases, make such installations unnecessary. The covering may be held at the surface onto which it has been placed by the employment of nails, glue, tape, such as adhesive tape, screws, or by any other suitable means for holding a sheet formed body onto a surface as known in the art. Means which are affecting the surface to a minimal extent, and which are easily removable, are preferable. The carrier may be a thin paper sheet, similar to wall paper, onto which the trapping agent is applied, such as by painting, smearing, or impregnating, before placement of the thus formed covering onto the surface from which undesired emissions are released.

The trapping agent is preferably able to trap different types of emissions, such as for example emissions that occur in water damaged buildings. Since it is yet not fully understood which specific emissions cause the noticed irritating, odouros or adverse health effects in e.g. water damaged buildings, it is preferable that the trapping agent may trap a wide spectrum of emissions, including e.g. particles or gaseous compounds. The trapping agent of the covering is preferably a substantially irreversible trapping agent. Hence, it may not allow any significant release of any trapped emission back to the air. One advantage of such an irreversible trapping agent is the minimized risk of exposure to hazardous emissions upon handling of the covering according to the invention after use for trapping of such emissions, or when a person is being in the vicinity of the same. The trapping agent may be a single compound or substance, or it may consist of a mixture of several compounds and/or substances. These may independently be covalently bond to the carrier or by any other way, as known in the art, suitably immobilized or placed on the carrier, such as adhered thereon. The trapping agent is thus held by the carrier, preferably to such a degree that the former is not released from the latter upon handling, in particular removal, of the covering, in order to minimize the risk of exposure to the trapping agent or, in particular, emissions held by the same. Preferably, the carrier is porous with the trapping agent immobilized on the full, or at least a part, of the inside surface of the pores. Advantageously, the carrier may thus allow water vapor to pass from the surface through the pores of the carrier while still allowing trapping of emissions by the exposed large surface area of the trapping agent. The size of the pores, after immobilization of the trapping agent, is preferably such that water vapor may still pass while still allowing the trapping agent to effectively come in contact with and trap emissions. The minimum average size of the pores, after immobilization of the trapping agent, may be 50 Å. In order to keep a sheet formed carrier as thin as possible while still allowing effective trapping of emissions, the maximum average size of the pores may be 0.05 mm.

The mechanisms by which the trapping agent traps the emission include absorption, sorption or adsorption or any other mechanism for trapping an emission based on molecular interactions as known in the art. Preferably, the trapping agent comprises one or several absorbing or adsorbing agents. Preferably, the absorbing or adsorbing agents may trap the emissions substantially irreversibly.

The surface from which the covering prevents or reduces emissions may be, but is not limited to, any inner surface of a construction used to house or shelter living beings, such as humans or animals. The surface may also be an inner surface of a construction which is linked to an accommodation for humans or animals, such as a ventilator, the inside of a wall or floor, floor joist systems, basements, crawlspaces, spaces above a ceiling, or any other construction from which emissions may reach the accommodation via the air. The surface may contain chinks or narrow openings e.g. at skirting boards, cornices etc, as well as smaller or larger cavities and openings, for example deliberately made as a step in a mold remediation process, through which emissions may pass e.g. into an indoor environment unless the emissions are hindered by the covering of the invention. Hence, emissions from the construction linked to the accommodation may pass to the accommodation when released into the space encompassed by the construction, unless this release is prevented or decreased by e.g. the covering of the invention. Surfaces from which the covering may prevent emissions include, but is not limited to, surfaces which have been exposed to smoke from fire or tobacco smoking, surfaces with proven or suspected microbial growth, surfaces in water damaged buildings, surfaces which have been treated with potential aggressive chemicals, surfaces which face a risk of mould growth, such as dead-ended floors or in the attic, surfaces in bathrooms or swimming baths, freshly painted surfaces, or surfaces in hospitals, such as in particular surfaces in intensive care units and surgery rooms. Additional surfaces include surfaces from which hazardous emissions including hormone disruptors such as bisphenol A, phthalates, alkyl phenols and flame retardants, may be released.

The carrier may be sheet formed with a first side and an opposite second side. The first side is for application on the surface from which emissions are released. The first side is then facing the surface and the second side is facing away from the surface. Preferably the carrier is flexible to allow the covering to attain essentially the same shape as the surface upon which it is placed. The carrier may be formed as sheets similar to wallpaper, which are flexible and which may be cut as desired. One advantage of such flexibility is the saving of space in e.g. a room a non-flexible covering would otherwise occupy when placed over a surface which was of a different shape. The carrier may be removable from the surface, whereby the covering may be removed after having been used. The surface may, for example, no longer give off unacceptable emissions and it is thus unnecessary for the covering to remain on the surface after it has filled its purpose to trap emissions. The trapping agent of the covering may also be saturated with trapped emissions. At that point in time, it is preferable to remove the covering and replace it with a new covering of which the trapping agent is not saturated. Preferably the appearance of the underlying surface is left unaffected or affected only to a slight degree upon applying and/or removing the covering onto/from the surface. The removed covering may contain trapped hazardous emissions and is therefore preferably handled and destructed in a suitable way as known in the art. The removed covering may, for example, be destructed in an environmentally friendly way, such as by combustion at a high temperature. Hence, a possibility exists to take care of the hazardous emissions in a suitable secondary step, e.g. combustion of the used covering, which is preferable over e.g. chemical decomposition of the emissions induced by the covering or the like, which may result in the formation of hazardous decomposition products readily reachable by people nearby.

The covering may also be provided with a semi-permeable barrier applied to the surface of the carrier, preferably to the second side of the carrier which is facing away from the surface onto which the covering is applied. The semi-permeable barrier may be e.g. a sheet formed structure with properties suitable for enhancing the functioning of the covering. Examples of materials suitable for production of the semi-permeable barrier include a suitably modified cellulose, such as a cellophane, e.g. Cellophane 335 PS which may be purchased from Innovia Ltd., or any other material known in the art to slow the rate through which e.g. volatile organic compounds (VOCs) are permeating.

Suitable means for attaching the semi-permeable barrier to the carrier include e.g. gluing, sewing, stapling, heat sealing, use of an adhesive tape, or any other suitable well known means. Preferably, the semi-permeable barrier is applied to the side of the carrier which is opposite the side from which one or several emissions are expected to enter the carrier. For example, when the covering is applied to a mould-infested wall to prevent emissions to enter the room adjacent to this wall, the carrier side of the covering may be facing the wall and the semi-permeable barrier side of the covering may be facing the room. The semi-permeable barrier may constitute a hindrance for various kinds of emissions. Emissions in the form of particles, such as microbial particles containing bacterial and fungal toxins, such as mycotoxins, may not be able to pass the semi-permeable barrier. For example, the pore-size of the semi-permeable barrier may be smaller than the particles. The particles are thereby trapped on the carrier side of the semi-permeable barrier by filtration. Emissions in the form of gaseous organic compounds or volatile organic compounds (VOCs), such as e.g. organic compounds with a boiling point in the range from 50° C. to 260° C., may generally not be trapped, at least not irreversibly, by the semi-permeable barrier. The effect of the semi-permeable barrier, on this type of compounds, may rather be to increase the residence time of these within the carrier. Because the permeability of these compounds through the semi-permeable barrier is less than the permeability in the open atmosphere, the medium residence time in the carrier of the molecules of a compound is increased in comparison to the case of a covering without a semi-permeable barrier. Such an increased residence time results in an increased probability of the trapping agent, which is residing in the carrier, to bind the compound, and thus to an increased efficacy of the covering. The semi-permeable barrier may thus be sheet formed and preferably cover a substantial part, such as the entire area or at least 90% of the area, of the carrier, in order to maximize this effect. Additional organic compounds, for which the residence time within the carrier may be increased by the semi-permeable barrier include, but is not kited to, organic compounds produced by microorganisms including bacteria, fungi or mould, secondary metabolites of such microorganisms, degradation products of construction materials which are unrelated to growing microorganisms, organic compounds emitted from paints, organic compounds emitted from surfaces which have been exposed to smoke from fire or tobacco smoking, organic compounds known or suspected to act as hormone disruptors, organic compounds used to impregnate materials or treat materials e.g. during remediation after water-damage, organic compounds having an unpleasant odour, irritating or unpleasant compounds, toxins, organic compounds formed upon the action of water on impregnated wooden materials, organic compounds formed by hydrolysis of glues and plasticizers, organic compounds occurring in water damaged buildings, organic compounds that originate either from growing microorganisms or from water acting on building materials followed by one or several secondary reactions, aldehydes, terpenes, furans, glycol ethers, ketones, alcohols, sulfides, disulfides, organic compounds with a molecular weight in the range from 16 to 1500 g/mol, allergens, or organic compounds which are odorous, irritating or harmful to the health of humans or animals. In addition, a semi-permeable barrier may not only assist in the trapping of the emissions from a surface, but may also prevent the covering from being loaded with VOCs from the outer side, such as room air; this will improve the capacity and lifetime of the covering.

Application Areas

The covering of the invention may be used in many different application areas as already described herein or as readily understood by the one skilled in the art.

An example of such an application area is remedial of water-damaged buildings: (i) Before remedial, the covering of the invention may be used to stop moisture-associated emissions until the surface is dry and the emissions have been reduced. In some cases further remediation may be unnecessary. (ii) During remedial, a fan used to dry a wet surface may be placed between the surface and the covering of the invention which may be formed as a "tent". The fan dries the surface while the water vapor escapes through the covering. The covering captures VOCs and particles, for example dirt and moulds, which may be emitted from the contaminated surface, and purifies in this way the air by preventing such particles and compounds from entering the room where people reside. (iii) After remedial, the covering of the invention may be placed at the surface immediately after the surface has been treated with sanitation agent(s). By this means, emissions caused e.g. by bleach, which are known to cause respiratory problems upon inhalation, as well as additional emissions released from the building materials due to adding the water at the remediation, may be stopped. Notably, recent research has revealed that mycotoxins are not deactivated by any of the sanitation methods in common use. The covering of the invention may stop or at least reduce the level of any mycotoxin. The covering, attached to the ceiling of a crawlspace, may also stop unpleasant odours which may be emitted from the crawlspace several weeks after mold remediation. Advantages of the covering according to the invention include that affected individuals can remain longer in the building (home, school, kindergarten, workplace etc) before the remediation and, if they have to leave for a shorter or longer period of time, move back home earlier.

Additional applications of the covering of the invention include, but are not limited to, the following:

(i) Surfaces frequently emit unpleasant odors after being exposed to smoke from a fire. These odors may be stopped or diminished by attaching the covering at the affected surfaces. (ii) Materials that have been pressure-creosoted or treated for example with cuprinol or other sanitation chemicals emit odors which may be unhealthy or highly unpleasant. Houseowners may choose to remove the affected building construction details. This may be avoided by using the covering of the invention. (iii) Unpleasant odors may also be emitted from concrete floors upon water-damage e.g. due to hydrolysis of carpet glue. This is a very wide-spread problem. The covering may stop or diminish such odors thus representing a cheaper and more convenient sanitation than mechanically removing large amounts of the concrete, which is a very laborious and expensive procedure. (iv) Surfaces which just have been painted emit VOCs which may be both unpleasant and unhealthy. Surfaces may continue to emit VOCs from the paint long after the painting. The covering may be used to stop such unwanted emissions. It may be adapted at the surface immediately after the painting is finished and allowed to stay there until emission rates are substantially decreased.

The Trapping Agent

According to one embodiment, the trapping agent is capable of trapping emissions produced by microorganisms that thrive at the humid conditions following water damage of building materials, buildings or houses.

According to one embodiment, the trapping agent is capable of trapping emissions produced by bacteria and/or fungi, such as molds, including proteins, glucans, enzymes, protein allergens, peptidoglycans, mycotoxins, endotoxins or exotoxins.

According to one embodiment, the trapping agent is capable of trapping emissions produced by microorganisms typically encountered in water damaged buildings including, for example, species of *Chaetomium, Alternaria, Penicillium, Streptomyces, Mycobacterium, Stachbotrys, Cladosporium, Fusarium*, or *Aspergillus*, or particles comprising these microorganisms.

According to one embodiment, the trapping agent is capable of trapping toxins produced by bacteria or mould, including valinomycin (of e.g. *Streptomyces* spp), endotoxins, protein exotoxins, secondary metabolites including mycotoxins such as gliotoxin, aflatoxins, patulin, trichotecenes such as T2 toxin, satratoxins or roridin, or sterigmatocystein, verrucarin J, citrinin, chaetoglobosin A, trichodermin, trichodermol, meleagrin, or roquefortine C.

According to one embodiment, the trapping agent is capable of trapping emissions which are irritating to nose and mucous membranes and related to microbial growth, including geosmin, 1-octene-3-ol, 3-octanone, 2-methyl-isoborneol, 2-octen-1-ol, or 3-methyl-1-butanol.

According to one embodiment, the trapping agent is capable of trapping emissions with unpleasant odours.

According to one embodiment, the trapping agent is capable of trapping emissions which are irritating to nose and mucous membranes including chlorinated anisols, formed upon the action of water on impregnated wooden materials, such as wooden materials impregnated with chlorophenols.

According to one embodiment, the trapping agent is capable of trapping emissions which are irritating to nose and mucous membranes and formed by hydrolysis of glues or plasticizers.

According to one embodiment, the trapping agent is capable of trapping emissions which are irritating to nose and mucous membranes and originate from chemicals used to treat materials e.g. during remediation after water-damage.

According to one embodiment, the trapping agent is capable of trapping emissions which originate from paints and from surfaces which have been exposed to smoke from fire or tobacco smoking.

According to one embodiment, the trapping agent is capable of trapping emissions that originate either from growing microorganisms, or from water acting on building materials, followed by one or several secondary reactions, such as reactions with ozone. For example, reactions with ozone results in the formation of hazardous free radicals and additional products formed from these. Compounds participating in such secondary reactions include e.g. alcohols, aldehydes, ketones, furans, glycol ethers or terpenes.

According to one embodiment, the trapping agent is capable of trapping hazardous emissions including hormone disruptors such as bisphenol A, phthalates, alkyl phenols and flame retardants.

According to one embodiment, the trapping agent is capable of trapping emissions independently selected from one or several of the group consisting of: aldehydes, such as formaldehyde, terpenes, such as α-pinene, β-pinene and limonene, furans, such as 3-methylfurane, glycol ethers, ketones, such as 2-butanone, 2-hexanone and 2-heptanone, alcohols, which may be short- or long- straight or branched including 2-ethylhexanol, 2-pentanol, all isomers of butanol and substituted butanols, disulfides, such as dimethyldisulfide, sulfides, such as methylmercaptane and dimethylsulfide, and organic compounds which may be e.g. volatile or semi-volatile with a molecular weight in the range from 16 to 1500 g/mol, chemicals containing e.g. boron and chloro or chloride (i.e. chemicals comprising covalently or ionically bond chlorine) used in remediation of water-damaged buildings, allergens, emissions generated by mould or bacteria or other compounds or particles which are irritating, unpleasant and/or harmful to the health of humans or animals.

According to one embodiment, the trapping agent is either an absorbing agent or an adsorbing agent, or consists of a mixture of at least one absorbing agent and at least one adsorbing agent. The choice of suitable absorbing or adsorbing agents depends on the nature of the emissions which are to be trapped by the trapping agent. In this choice, the one skilled in the art may begin by classifying each emission according to the most suitable, or at least suitable, molecular interactions which could be employed for trapping each emission. Thereafter, the skilled person may select agents, such as absorbing agents or adsorbing agents, which are capable of acting as counterparts in such molecular interactions. For example, emissions consisting of highly non-polar, i.e. fat soluble, organic molecules may be trapped in accordance with the generally known principle "fat dissolves fat". A non-polar absorbing agent, such as a long straight chain hydrocarbon with a suitable functional group, such as a carboxylic acid, for immobilization onto the surface of the carrier, may be chosen as a major or minor constituent of the trapping agent for trapping of highly non-polar organic molecules. Other molecular interactions which may be employed for the choice of trapping agents include, but is not limited to acid-base interactions, dipole-dipole interactions, hydrogen bonding, ionic interactions, non-polar interactions, enzyme-substrate bonding, antibody-antigen interactions, receptor-ligand interactions, metal-ligand binding, size and shape dependant molecular inclusions, or aromatic interactions. All of these molecular interactions are herein to be understood as comprised by the term "adsorption". An adsorbing agent may thus trap emissions by one or several of above mentioned molecular interaction, or by any other way or ways of adsorption as well known to the skilled person.

According to one embodiment, the trapping agent may be independently selected from, but is not limited to, one or several of the group consisting of carbon based adsorbents, such as activated carbon, charcoal or the Carbopak® series, porous polymers, such as the Chromosorb® series, the Porapak® series, the Tenax® series, the HayeSep® series, the XAD® series, clays, diatomaceous earth, magnesium silicates, such as Florisil®, ashes, micronized silicon dioxide, christobalite, hydrated sodium calcium aluminosilicates, chitosan, granulas, anionic ion exchange resins, cationic ion exchange resins, modified ion exchange resins, zeolites, perlite, bentonite, $C_{4-30}$ aliphatic hydrocarbons, $C_{4-30}$ unsaturated hydrocarbons, gas chromatography stationary phases, liquid chromatography stationary phases, polyethylene glycol with a melting point in the range from 30 to 100° C., preferably 40 to 50° C., silica gel, aluminum oxide, cellulose, granulates, high boiling liquids such as polysiloxanes, phenyl substituted stationary phases, bases, acids and diethylene glycol succinate derivatives.

According to one embodiment, the trapping agent may comprise one or several chemosorbents, such as for example KOH, $KMnO_4$, phosphoric acid and metal oxides, as well known in the art. Advantages of such chemosorbents include a greater trapping capability of the trapping agent of emissions such as e.g. nitrogen-containing compounds, aldehydes, amines and acids. Chemosorbents of the kind mentioned herein above may not be combined with some types of trapping agents mentioned herein due to e.g. their oxidizing properties. The various kinds of combinations between chemosorbents and other trapping agents that may or may not be done, are well known to the one skilled in the art.

The Carrier

According to one embodiment, the carrier may have a suitable porous structure in the form of sheets with a thickness of 0.1 to 10 mm. These sheets are preferably foldable into e.g. rolls for easy transportation and may be cut in suitable shapes for application onto a surface, similar to wallpaper. A suitable porous structure may allow the trapping agent to be immobilized therein. The porous structure may preferably allow the passage of water in gaseous form there through while simultaneously holding the trapping agent immobilized.

According to one embodiment, the carrier may be selected from the group consisting of: cellulose containing materials such as paper, modified cellulose containing materials where the hydrogen of one or several hydroxyl groups have been replaced by carbon containing groups, natural and synthetic fibres and textiles, glass fibers, mineral wool fibers, nanofiber materials, nonwoven materials for example materials which are spunbond, wetlaid, spunlace or thermobonded used e.g. in products such as Tyvek (a brand of flashspun polyethylene fibers), GoreTex (expanded polytetrafluoroethylene) or nonwoven materials such as those used for air filtration etc, porous plastic materials or other suitable polymers, or other materials, as known in the art. The carbon containing groups, which have replaced the one or several hydroxyl groups, may constitute, comprise or have the full or partial function of the trapping agent.

According to one embodiment, a suitable adhering agent, such as calcium hydroxide, may aid the adhering, i.e. immobilization, of the trapping agent to the carrier. Other methods, such as heat-sealing, and adhering agents such as glues, pliolite resins or the like, and their corresponding suitable amounts, are well known in the art. The adhering agent may have no or some capability to trap emissions. In the case the adhering agent has such a capability it has a dual function, it aids the immobilization of the trapping agent and simultaneously aids the latter in the trapping of emissions. The adhering agent's ability to trap emissions may be complementary to the trapping agent and thus trap emissions not effectively trapped by the latter. For example, sodium bicarbonate may serve as an adhering agent while simultaneously transforming gaseous acids into their corresponding salts and thereby aiding the trapping of these.

According to one embodiment, the trapping agent may be applied to the carrier to form the covering just prior to use of the latter. The trapping agent may also be applied to the carrier long before use, such as days, weeks, months or years. The trapping agent as well as the covering may be kept in, for example, a closed can in order to better preserve their capabilities to trap emissions over long term storage, such as storage over such as days, weeks, months or years.

According to one embodiment, the carrier may constitute a significant hindrance for oxygen, such as oxygen in the air. A covering comprising such a carrier thereby attains the property of allowing no, or only minimal, passage of oxygen. This feature may advantageously, after the covering has been attached at e.g. a mold-infested surface, using e.g. an adhesive tape, limit mold growth.

According to one embodiment, the carrier may be highly permeable to air. Such a carrier may be chosen in cases when it is important e.g. not to hinder the drying of a moist surface by using fans.

According to one embodiment, the covering may be one single material with properties, as disclosed herein, of both a trapping agent and of a carrier. An example of such a material includes, but is not limited to, e.g. a carbon cloth. Hence, the covering may comprise a single piece of a material that combines the functions of the carrier and the trapping agent(s) at the same time. New materials with e.g. new properties, suitable for ensuring a satisfactory or improved functioning of the covering, may be developed, as known in the art, by employment of e.g. nanotechnology with and without the use of nonwoven materials. An advantage of a material with such a combined function includes the absence of the need to assemble a separate carrier and a separate trapping agent to get a covering. Hence, a covering comprising a material with the combined function is produced in a more cost effective way in comparison to the case with a covering comprising a separate carrier and a separate trapping agent.

According to one embodiment, the carrier may in itself possess some or all of the properties of a suitable semi-permeable barrier as described herein. In such cases, the trapping agents may be directly attached to the carrier/barrier, such as to a carrier/barrier sheet, to form the covering. Advantageously, no separate semi-permeable barrier or carrier are thus necessary for the manufacturing of the covering, which is more cost effective.

According to one embodiment, the covering may also comprise a single sheet of a material that combines the functions of the carrier, trapping agent(s), and semi-permeable barrier at the same time. Such materials may be developed e.g. using nanotechnology based upon nonwoven or other materials.

The Semi-Permeable Barrier

According to one embodiment, the semi-permeable barrier may constitute one layer of the covering. The other layer of the covering may be constituted by the carrier and the trapping agent. An advantage of a covering which comprises a semi-permeable barrier is an increased efficacy to trap emissions such as volatile organic compounds.

According to one embodiment, the semi-permeable barrier may be permeable to water vapor. A damp wall onto which the covering of the invention is applied may then be dried without having to remove the covering, provided that the carrier is also water vapor permeable to, at least, some extent.

According to one embodiment, the semi-permeable barrier may constitute a significant hindrance for oxygen, such as oxygen in the air. A covering comprising such a semi-permeable barrier thereby attains the property of allowing no, or only minimal. passage of oxygen. This feature may advantageously, after the covering has been attached at e.g. a moist and/or mold-infested surface, using e.g. an adhesive tape, limit mold growth.

According to one embodiment, the semi-permeable barrier may be permeable to a high extent to air including oxygen. A covering comprising such a semi-permeable barrier thereby attains the property of allowing passage of air/oxygen, provided that the carrier is also permeable to a high extent to air including oxygen. Such a high permeability to air/oxygen is beneficial for the exchange of air in e.g. a room with walls onto which the covering has been applied or when fans are used to dry a damp wall.

According to one embodiment, the semi-permeable barrier may simultaneously constitute a significant hindrance for oxygen, such as oxygen in the air, and have good permeability for water vapor. An advantage of such combination of features is limitation of mold growth while still allowing drying of a damp wall onto which the covering has been applied. An example of a suitable material with such combined features is Cellophane 335 PS, which may be purchased from Innovia Ltd. This cellophane is an efficient barrier to air/oxygen and VOCs, but is readily permeable to water vapor. Other materials with similar combined features include e.g. suitable nonwoven materials.

According to one embodiment, the semi-permeable barrier may simultaneously have good permeability for both air and water vapor but not for VOCs. It may, for example, be made of a suitable nonwoven materials such as those used for air filtration. Such a barrier may preferably be used e.g. in order not to reduce the efficiency of the drying process when a fan is used to dry a moist surface.

According to one embodiment, the semi-permeable barrier may be porous. Advantages of a porous semi-permeable barrier include e.g. the simultaneous presence of a high water permeability and low permeability of volatile organic compounds. The size of the pores are preferably optimized to allow for rapid passage of the relatively small water molecule, but not molecules of relatively larger volatile organic compounds, as well known in the art.

According to one embodiment, the semi-permeable barrier may be made of a substantially homogenous material, e.g. a non porous material. Molecules, e.g. VOCs, water or oxygen, would have to pass such a homogenous material substantially by diffusion, in contrast to a porous material, through which molecules may pass via passages through the pores. An advantage of the employment of a homogenous material, e.g. a sheet, as a semi-permeable barrier, is the possibility for designing its selectivity on basis of molecular interactions as well known in the art, and not primarily on the size of the molecules which are to be discriminated.

According to one embodiment, the semi-permeable barrier may not be permeable, or only permeable to a less extent, to oxygen. The microbial growth within e.g. a wall, onto which the covering of the invention has been applied, may thereby be reduced. Associated emissions are thereby also reduced.

According to one embodiment, the semi-permeable barrier may be made of, for example, nonwowen materials for example materials which are spunbond, wetlaid, spunlace or thermobonded used e.g. in products such as Tyvek (a brand of flashspun polyethylene fibers), GoreTex (expanded polytetrafluoroethylene), or air-permeable nonwoven materials such as those used for air filtration etc, allowing passage of water vapor, at the same time being efficient barriers for liquid water as well as for VOC and air (types Tyvek and GoreTex) or for liquid water and VOC (type nonwovens used for air filtration) regenerated cellulose, or any other material from which a semi-permeable barrier with properties which will enhance the performance of the carrier and the trapping agents may be produced.

According to one embodiment, the semi-permeable barrier may be made of cellulose, or chemically modified or regenerated cellulose such as cellophane, which is a renewable and environment-friendly product.

According to one embodiment, the semi-permeable barrier may be made of a suitable material originating from viscose such as cellophane, for example Cellophane 335 PS from Innovia Ltd, a product usually applied in the bakery industry for the wrapping of bread. Advantages of materials originating from viscose include their high availability and relatively low cost.

According to one embodiment, the semi-permeable barrier may be sheet-formed with a thickness of 0.001-1 mm.

According to one embodiment, the semi-permeable barrier may be thinner than the carrier onto which it is applied. The thickness of the semi-permeable barrier may be 1 to 90%, such as 10 to 80 or 20 to 70%, of the thickness of the carrier. Advantages of having a semi-permeable barrier which is thinner than the carrier include, for example, a greater capacity per length unit of the total thickness of the covering to contain trapping agent.

Method

According to one embodiment, a method for use of a covering for reduction or prevention of a singularity or a plurality of emissions released from a surface is disclosed. The covering as described herein, essentially comprises a trapping agent as described herein. The method essentially comprises the step of: (i) applying, fastening or adhering an absorbing agent or an adsorbing agent, such as the covering of the invention comprising such agent(s), onto the surface, such that the surface becomes partly or fully coated with the absorbing agent or adsorbing agent, or with the covering. The emissions originating from the surface are thereby trapped by the absorbing agent or adsorbing agent, or by such agents in the covering. The method may further comprise applying, fastening or adhering a semi-permeable barrier to the carrier of the covering, such as on the side of the carrier which is opposite the side of the carrier which is facing the surface. The surface, such as for example an inner wall of a building or a room, may be flat, planar or curved. It may comprise various irregularities such as bulges, inward bends, holes, cracks, gaps, slots and stationary mounted objects such as e.g. power outlets. The covering is preferably flexible to allow a tight fit over a curved or planar surface and a smooth transition between the surface and an outwards pointing irregularity of the surface. If the irregularity is a hole or crack located within the borders of the surface, the covering will encompass it automatically as the covering is fastened to the surrounding surface. Emissions transferred via e.g. a hole or a crack by being connected to e.g. a separate volume or room from which the emissions are originating, are thus prevented from entering the volume, e.g. a room, which is defined, fully or partly, by the surface. Preferably, the covering is loosely fixated around a hole or crack to allow emissions steaming there from to be exposed to a larger area of the covering as compared to the case when the covering is tightly fixated over the hole or crack. Such a loose fixation allows for longer usage of the covering by elongating the time until saturation of the trapping agent. If the irregularity is constituted by e.g. a slot at the border of the surface, the covering is preferably fastened at the nearest subsequent surface. For example, in order to cover a slot between the lower part of a wall, which is constituting the surface to be coated with the covering, and the floor, the lower end part of the covering is preferably fixated to the floor.

According to one embodiment, a method for the manufacturing of a covering according to the invention is provided. The method comprises the steps of: (i) coating the surface of the carrier with a suspension or solution of the trapping agent in a solvent or liquid, (ii) allowing the solvent or liquid to evaporate to leave the trapping agent adhered to the carrier. The method may further comprise the step of applying, fastening or adhering a semi-permeable barrier, preferably as a sheet, to the surface of the carrier. Preferably to the side of the covering or carrier which will not be facing the surface from which emissions are released. The carrier may be, for example, a sheet of paper similar to wall-paper. The solvent or liquid may be, for example, water. A suitable adhering agent, such as calcium hydroxide, may be added to the suspension or solution in order to aid the adhering of the trapping agent to the carrier. Other adhering agents, such as glues, pliolite resins or the like, and their corresponding suitable amounts, are well known in the art. Heat-sealing may also be applied.

The carrier may be coated or impregnated with the suspension or solution of the trapping agent either on the side that is facing the surface from which the emissions are released, on the opposite side, or on both sides. In the case the trapping agent is a liquid, or may be heated to become a liquid, the trapping agent may be applied to the surface in step (i) without the need of a solvent or liquid for the formation of a suspension or solution.

According to one embodiment, another method for the manufacturing of a covering according to the invention is provided. The method comprises the steps of: (i) coating the surface of the carrier with a suitable adhering agent, such as a suitable glue, e.g. glue of a type normally used for wallpapers, (ii) spreading the trapping agent on the surface of the carrier which is coated with the adhering agent so that the trapping agent adheres thereto.

According to one embodiment, yet another method for the manufacturing of a covering according to the invention is provided. The method comprises applying to the surface of the carrier in a dry form the trapping agent in a dry form, such that the trapping agent becomes adhered to the carrier. Ways for adhering a trapping agent to a carrier are known in the art and include spreading of a fine dust with or without the employment of electrostatic techniques.

According to one embodiment, the semi-permeable barrier may be adhered to the carrier by using heat-sealing or glue. The spots of glue or seal may preferably be small (typically <5%) in comparison to the total area of the covering with e.g. approximately 5 cm between the spots.

EXAMPLES

The following examples serve to illustrate embodiments of the invention:

Example 1

Reduction of the Emission of 1-octene-3-ol from a Wood Surface

Pieces (10×10 cm) of Masonite® were soaked in a solution of 1-octene-3-ol in water (1004 μL/500 ml) for 30 min and then stored for 24 h at room temperature to obtain soaked Masonite®. Two tablespoonful of finely divided XAD®-2 (a hydrophobic crosslinked polystyrene copolymer resin), four tablespoonful of activated carbon, and five tablespoonful of $Ca(OH)_2$ was mixed and then suspended in a cup of water. One thin sheet of paper was painted with the obtained suspension, immediately followed by powdering with activated carbon on the wet surface, to obtain treated paper. One soaked piece of Masonite® was covered with treated paper, with the painted side of the paper facing the Masonite®, to obtain paper covered Masonite®. One piece of soaked Masonite®, and one piece of paper covered Masonite® were, 24 h after preparation, each placed in an individual container through which air was pumped at 2 l/min for 10 min. according to a standard method. The outgoing air was led through sampling tubes provided by and analyzed by Chemik AB, Sweden. The analysis of these tubes showed that the emission of 1-octene-3-ol into the surrounding air was decreased by 97% (paper covered Masonite®) in comparison to the Masonite® (soaked Masonite®) which had no type of emission preventing covering.

Examples 2 to 4

Reduction in Particulate and Vaporous Emissions from Solid and Liquid Surfaces

In Examples 3 to 4 below, the covering was in the size of 0.1×0.2 m. A 0.3-mm thick glass fiber sheet, purchased at a local store, was used as the carrier. The trapping agent(s) consisted of 2.2 g of a mixture of commercially available ingredients: Pellets of activated charcoal purchased from Sigma (70%), amberlite XAD-4 purchased from Sigma (10%), and Zeocat z-400 zeolite (1.2-2 mm pellets) purchased from ZeoChem (20%). The trapping agent mixture was attached to the glass fiber sheet by using a thin layer of spots of wallpaper glue purchased at a local store. The barrier consisted of a cellophane sheet with high permeability for water vapor and low permeability for air (including oxygen) and VOC (Cellophane 335PS, purchased from Innovia), and was attached to the glass fiber sheet by small spots of the glue every 5 cm; the trapping agents were situated between the glass fiber sheet and the cellophane sheet. Some experiments were performed after the semi-permeable barrier/cellophane sheet had been removed from the covering, or by using the barrier only. In Example 2 the covering was used as described above, but shaped as a circular surface with 37 mm diameter and containing 0.01 g of the trapping agent mixture.

Example 2

Comparison Between the Presence and the Absence of a Semi-Permeable Barrier of the Covering in the Reduction of Emissions of Mycotoxins Generated by *Aspergillus Versicolor* from a Paper Surface A culture of *Aspergillus versicolor* (a mold frequently found in water-damaged buildings and known to produce sterigmatocystein, a carcinogenic mycotoxin) was kept on a piece of air-permeable paper in a desiccator for 24 h. Then the paper together with the mold was placed in the lower position of a 37 mm Casella cassette, the covering with or without the semi-permeable barrier was placed in the middle position, and a Teflon filter (0.4 um pore size) was placed in the highest position. When the semi-permeable barrier was included it was positioned in such a way that it constituted the upper part of the covering, thus facing the Teflon filter In each experiment, air was pumped through the cassette at 250 ml/min for 15 min with the airflow in direction from the lower to the upper part of the cassette. Then the Teflon filter was extracted by methanol and analyzed by high performance liquid chromatography-tandem mass spectrometry.

When the covering was used without the semi-permeable barrier, 2 ng of sterigmatocystein were found on the Teflon filter. By contrast, sterigmatocystein was not found when the semi-permeable barrier was present. These results show that the covering with, but not without, the semi-permeable barrier can stop surface emissions from aerosolized particles which may contain mycotoxins.

Example 3

Reducing VOC Emissions from an Aqueous Surface by the Covering

The following volatile organic compounds (VOCs) were selected as model emission substances because they are commonly found in indoor air of water-damaged buildings and are both of microbial and non-microbial origin. The substances represent different chemical classes of compounds and include both smaller and larger molecules to illustrate the versatility in the performance of the covering.

Aqueous solutions of the following chemicals were used:
Solution 1 contained acetone (10 uM), 2-methyl-1-propanol (20 uM), benzene (10 uM), ethyl acetate (10 uM), 2-methylfuran (15 uM), 1-propanol (30 uM), and 1-methoxy-2-propanol (30 uM).

Solution 2 contained 1-butanol (40 uM), 3-methyl-2-butanol (10 uM), 3-methyl butanol (100 uM), dimethyl disulphide (15 uM), hexanal (50 uM), 2-heptanone (50 uM), styrene (50 uM), anisole (40 uM), alpha-pinene (10 uM), 1-octen-3-ol (40 uM), benzaldehyde (70 uM), 2-ethyl-1-hexanol (50 uM), and limonene (15 uM).

Of each solution, a 100-ml aliquot was transferred to a plastic box which was then closed with a lid with a 14-cm long and 1-cm wide slit. In subsequent experiments, the slit was either covered using the covering (attached by an adhesive tape), the covering without the semi-permeable barrier, only the semi-permeable barrier, or left open. The container was stored in separate locations for up to 120 h and then placed in a closet where, after different time intervals, air samplings were performed during 30 min through a cartridge containing either Tenax (Solution 1, sampling at 100 ml/min following thermal desorption and gas chromatography-mass spectrometry [GC-MS] analysis at IVL in Stockholm) or activated charcoal (Anasorb 747, purchased from SKC) (Solution 2, sampling at 250 ml/min following extraction with dichloromethane and GC-MS analysis at Lund University or at Pegasus lab, Uppsala). Notably, thermal desorption is preferred for the analysis of very small molecules, such as those included in Solution 1, which may be difficult to discern when analyzing solvent extracts with GC-MS. With the slit left uncovered, air concentrations of 10-111 ug/m$^3$ (toluene equivalents) of the chemicals were found. Closing the slit by the covering (including the barrier) resulted in a decrease according to the following (Solution 1 was studied after up to 24 h of storage whereas Solution 2 was studied after up to 72 h of storage):

For Solution 1 the reductions (%) 30 min and 24 h after closing the slit, respectively, were 90.0 and 93.5 (acetone), 99.9 and 99.9 (2-methylfuran), 99.9 and 99.9 (ethyl acetate), 99.2 and 99.5 (benzene), 99.6 and 99.6 (1-propanol), 99.5 and 99.2 (2-methyl-1-propanol), and 77.0 and 90.0 (1-methoxy-2-propanol).

For Solution 2 the reductions (%) 30 min, 24 h, 48 h, and 72 h after closing the slit, respectively, were 95.1, 97.4, 95.4, and 100 (1-butanol), 94.9, 91.0, 100.0, and 100 (3-methyl-2-butanol), 96.0, 98.3, 97.0, and 99.3 (3-methylbutanol), 88.4, 97.5, 99.6, and 99.9 (dimethyl disulphide), 81.6, 85.7, 86.5, and 90.2 (hexanal), 95.7, 95.8, 98.7, and 99.4 (2-heptanone), 81.3, 92.3, 97.6, and 98.0 (styrene), 92.8, 93.5, 98.2, and 99.2 (anisole), 81.7, 72.4, 71.9, and 85.9 (alpha-pinene), 99.1, 98.8, 96.5, and 99.4 (1-octen-3-ol), 97.5, 97.4, 95.9, and 97.8 (benzaldehyde), 98.1, 98.1, 98.1, and 98.9 (2-ethyl-1-hexanol), and 46.2, 89.4, 87.7, and 91.7 (limonene).

These results demonstrate clearly the efficiency of the covering in reducing emissions of a wide range of VOC from surfaces.

Example 4

Comparisons Between Use of the Covering with a Semi-Permeable Barrier, the Covering without a Semi-Permeable Barrier, and only the Semi-Permeable Barrier, for Reducing VOC Emissions from an Aqueous Surface These three experiments utilized Solution 2 and the general experimental set-up was as in Example 3 (see above). Experiments were performed by using the covering with the semi-permeable barrier, the covering without the semi-permeable barrier, and by using only the semi-permeable barrier.

Air samplings were performed 24 h after the covering with (B1) and without (B2) the semi-permeable barrier, respectively, had been attached at the slit. The relative air concentrations of the VOCs (ratios B2/B1) were 4.28 (1-butanol), 9.66 (3-methyl-2-butanol), 5.06 (3-methylbutanol), 4.34 (dimethyl disulphide), 1.90 (hexanal), 3.24 (2-heptanone), 6.55 (styrene), 4.06 (anisole), 1.03 (alpha-pinene), 1.17 (1-octen-3-ol), 1.44 (benzaldehyde), 1.03 (2-ethyl-1-hexanol) and 4.50 (limonene). These results clearly show that the barrier assists in reducing the air concentrations of the VOC.

The semi-permeable barrier (without trapping agents or carrier) was attached over the slit of one box (B1) and the covering (carrier, trapping agents, and semi-permeable barrier) was attached over the slit of a second box (B2). After 120 h the semi-permeable barrier and covering were removed and air sampling was performed. The air concentrations over B1 in relation to B2 (the B1/B2 ratios) were 1.9 (1-butanol), 2.7 (3-methyl-2-butanol), 2.1 (3-methylbutanol), 13.3 (dimethyl disulphide), 5.3 (hexanal), 6.5 (2-heptanone), 4.3 (styrene), 3.7 (anisole), 3.6 (alpha-pinene), 2.1 (1-octen-3-ol), 3.1 (benzaldehyde), 2.0 (2-ethyl-1-hexanol), and 1.6 (limonene). These results show that the barrier in itself may partly stop the VOCs, but only temporarily leading to re-emissions, whereas the combined use of the barrier and the adsorbents, i.e., the covering, binds the VOCs irreversibly.

In another experiment, the trapping agents were removed from the covering after the covering had been used to trap VOCs during 24 h, then, the trapping agents were extracted with dichloromethane and analyzed by GC-MS. One covering had been attached over the slit as recommended (with the trapping agents facing the slit, box B1) whereas the second covering had been placed upside down (with the semi-permeable barrier facing the slit, box B2). The amounts of the VOCs (picograms injected onto the GC-MS, toluene equivalents) from the B1 and B2 sample extracts, respectively, were 465 and 74.9 (1-butanol), 503 and 27.2 (3-methyl-2-butanol), 1470 and 150 (3-methylbutanol), 378 and 21.2 (dimethyl disulphide), 123 and 16.0 (hexanal), 1330 and 55.4 (2-heptanone), 1150 and 11.5 (styrene), 740 and 29.5 (anisole), 306 and 0 (alpha-pinene), 1280 and 83.1 (1-octen-3-ol), 1020 and 194 (benzaldehyde), 1260 and 60.7 (2-ethyl-1-hexanol), and 192 and 0 (limonene). These results show that the VOCs are trapped by the covering efficiently and that the semi-permeable barrier provides a hindrance for VOCs to permeate there through.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A covering for application on a surface and reduction or prevention of a singularity or a plurality of emissions released from said surface, said covering comprising:
   a trapping agent;
   a carrier for retaining and supporting said trapping agent, such that said trapping agent can trap said singularity or plurality of emissions without being released from said carrier,
   wherein said trapping agent includes an absorbing agent or an adsorbing agent, or a combination thereof, such that said trapping agent is capable of fully or partly trapping said singularity or plurality of emissions by absorption or adsorption, or by a combination of absorption and adsorption, and said carrier includes a sheet having a first side and an opposite second side, said first side is for application on said surface such that said first side is facing said surface and said second side is facing away from said surface; and a semi-permeable barrier on said second side, wherein said semi-permeable barrier is permeable to water in gaseous form, such that said covering can trap said singularity or plurality of emissions while said covering is simultaneously allowing escape of water in gaseous form from said surface, said semi-permeable barrier is non-permeable to oxygen, or permeable to only a low extent to oxygen, and said semi-permeable barrier is substantially homogeneous, such that molecules pass through said semi-permeable barrier by diffusion in the material said semi-permeable barrier is made of.

2. The covering according to claim 1, wherein said semi-permeable barrier is a sheet covering said second side.

3. The covering according to claim 1, wherein the thickness of said semi-permeable barrier is 0.001-1 mm, and wherein the thickness of said semi-permeable barrier is smaller than the thickness of said carrier.

4. The covering according to claim 1, wherein said carrier is flexible, such that said covering attains essentially the same shape as said surface when placed on said surface.

5. The covering according to claim 1, wherein said carrier is porous and at least a part of said trapping agent is immobilized on the inner surface of the pores of said carrier.

6. The covering according to claim 1, wherein said carrier is selected from the group consisting of cellulose containing materials, modified cellulose containing materials, textiles, natural fiber materials, synthetic fiber materials, nano fiber materials, nonwoven materials including materials which are spunbound, wetlaid, spunlace or thermobonded, air-permeable nonwoven-based materials, porous plastic materials, polymeric materials and monomeric materials.

7. The covering according to claim 1, wherein said covering is further comprising an adhering agent.

8. The covering according to claim 1, wherein said trapping agent is selected from the group consisting of carbon based adsorbents, poreous polymers, clays, diatomaceous earth, magnesium silicates, ashes, micronized silicon dioxide, christobalite, hydrated sodium calcium aluminosilicates, chitosan, granulas, anionic ion exchange resins, cationic ion exchange resins, modified ion exchange resins, zeolites, perlite, bentonite, $C_{4-30}$ aliphatic hydrocarbons, $C_{4-30}$ unsaturatedhydrocarbons, gas chromatography stationary phases, liquid chromatography stationary phases, polyethylene glycol, silica gel, aluminum oxide, cellulose, granulates, high boiling liquids, phenyl substituted stationary phases, bases, acids and diethylene glycol succinate derivatives.

9. The covering according to claim 1, wherein said semi-permeable barrier is made of cellulose, or chemically modified or regenerated cellulose.

10. The covering according to claim 9, wherein said semi-permeable barrier is made of cellophane.

* * * * *